United States Patent [19]

Blackburn, Jr. et al.

[11] Patent Number: 5,008,283
[45] Date of Patent: Apr. 16, 1991

[54] USE OF TENIDAP TO INHIBIT ACTIVATION OF COLLAGENASE AND TO INHIBIT THE ACTIVITY OF MYELOPEROXIDASE

[75] Inventors: Warren D. Blackburn, Jr.; Leland D. Loose, both of Groton, Conn.

[73] Assignee: Pfizer Inc., New York, N.Y.

[21] Appl. No.: 495,868

[22] Filed: Mar. 19, 1990

[51] Int. Cl.$^5$ .............................................. A01N 43/38
[52] U.S. Cl. ........................................ 514/414; 514/418; 514/912; 514/814; 514/415; 514/419
[58] Field of Search ................................. 514/414, 418

[56] References Cited

U.S. PATENT DOCUMENTS

| 4,556,672 | 12/1985 | Kadin | 514/414 |
| 4,725,616 | 2/1988 | Kadin | 514/411 |
| 4,853,409 | 8/1989 | Showell | 514/418 |
| 4,861,794 | 8/1989 | Otterness | 514/414 |
| 4,920,127 | 4/1990 | King et al. | 514/278 |

FOREIGN PATENT DOCUMENTS 277738 8/1988 European Pat. Off. .

OTHER PUBLICATIONS

CA: 110(21) 185555r.
CA: 110(25) 229951y.
Hasty, K. A. et al., "Secreted Forms of Human Neutrophil Collagenase", J. Biol. Chem. 261: 5645-5650 (1986).
Hasty, K. A., et al., "The Collagen Substrate Specificity of Human Neutrophil Collagense", J. Biol. Chem. 262: 10048-10052 (1987).
Harris, E. D. et al., "Collagenases (First of Three Parts)", NEJM 291: 557-563 (1974).
Harris, E. D. et al., "Collagenases (Second of Three Parts)", NEJM 291: 605-609 (1974).
Harris, E. D. et al., "Collagenases (Third of Three Parts)", NEJM 291: 652-661 (1974).
Goldstein, I. M., "Agents that Interfere with Arachidonic Acid Metabolism", *Inflammation: Basic Principles and Clinical Correlates*, Gallin, J. I., Goldstein, I. M., and Snyderman, R., Eds. (1988), pp. 935-946, Raven Press, New York.
Weiss, S. J. et al., "Oxidative Autoactivation of Latent Collagenase by Human Neutrophils", Science 227: 747-749 (1985).
Mallya, S. K. et al., "Mechanism of Inhibition of Human Neutrophil Collagenase by Gold (I) Chrysotherapeutic Compounds", J. Biol. Chem. 264: 1594-1601 (1989).
Mallya, S. K. et al., "Inhibition of Human Neutrophil Collagenase by Gold(I) Salts Used in Chrysotherapy", Biochem. Biophys. Res. Comm. 144: 101-108 (1987).
Cuperus, R. A. et al., "Antiarthritis Drugs Containing Thiol Groups Scavenge Hypochlorite and Inhibit its Formation by Myeloperoxidase from Human Leukocytes", Arthritis Rheum. 28: 1228-1233 (1985).
Genetic Engineering News, p. 11, Nov./Dec. 1989.
Havemann, K., et al., "Physiology and Pathophysiology of Neutral Proteinases of Human Granulocytes", Adv. Exp. Med. Biol. 167: 1-20 (1984).
Showell, H. J., et al., J. Reticuloendothelial Society 30: 167-181 (1981).
Showell, H. J. et al., Life Sciences 27: 421-426 (1980).
Walenga, R. W. et al., Life Sciences 27: 1047-1053 (1980).
Serhan, C. N. et al., Biochem. Biophys. Res. Comm. 107: 1006-1012 (1982).
Smolen, J. E., et al., "Effects of Indomethacin, 5,8,11,14-Eicosatetraynoic Acid, and p-Bromophenacyl Bromide on Lysosomal Enzyme Release and Superoxide Anion Generation by Human Polymorphonuclear Leukocytes", Biochem. Pharmacol. 29: 533-538 (1980).
Turner, R. A. et al., "Effects of Benoxaprofen on Human Neutrophil Function", J. Rheumatology 11: 265-271 (1984).
Mikulikova, D. et al., "The Effect of Indomethacin and Its Ester on Lysosomal Enzyme Release from Polymorphonuclear Leukocytes and Intracellular Levels of cAMP and cGMP After Phagocytosis of Urate Crystals", Biochem. Pharmacol. 31: 460-463(1982).
Edelson, H. S. et al., "Dissociation by Piroxicam of Degranulation and Superoxide Anion Generation from Decrements in Chlortetracycline Fluorescence of Activated Human Neutrophils", Biochem. Biophys. Resl. Commun. 104: 274-253 (1982).
Maderazo, E. G. et al., "Inhibition of Human Polymorphonuclear Leukocyte Cell Responses by Ibuprofen", J. Pharmaceutical Sciences 73: 1403-1406 (1984).
Simchowitz, L. et al., "Chemotactic Factor-Induced Generation of Superoxide Radicals by Human Neutrophils", Arthritis and Rheumatism, 22: 755-763 (1979).
Abramson, S. et al., "Modes of Action of Aspirin-Like Drugs", P.N.A.S. 82: 7227-7231 (1985).
Minta, J. O. et al., "Some Nonsteroidal Antiinflammatory Drugs Inhibit the Generation of Superoxide Anions by Activated Polymorphs by Blocking Ligand-Receptor Interactions", J. Rheumatol. 12: 751-757 (1985).

*Primary Examiner*—Stanley J. Friedman
*Assistant Examiner*—T. J. Criares
*Attorney, Agent, or Firm*—Peter C. Richarson; J. Trevor Lumb; Gregg C. Benson

[57] ABSTRACT

This invention relates to the use of tenidap, 5-chloro-2,3-dihydro-2-oxo-3-(2-thienylcarbonyl)-indole-1-carboxamide, and the pharmaceutically-acceptable base salts thereof to inhibit activation of collagenase in a mammal and to inhibit the activity of myeloperoxidase in a mammal. This invention also relates to the use of tenidap and its salts for treating collagenase mediated disorders and diseases such as bone resorption disorders, corneal ulceration, periodontal disease, inflammatory disease and wounds of the skin and burns in mammals. The methods of this invention comprise administering an effective amount of tenidap or salts thereof to a mammal.

21 Claims, No Drawings

USE OF TENIDAP TO INHIBIT ACTIVATION OF COLLAGENASE AND TO INHIBIT THE ACTIVITY OF MYELOPEROXIDASE

BACKGROUND OF THE INVENTION

1. Field of the Invention

This invention relates to the use of tenidap and the pharmaceutically-acceptable base salts thereof to inhibit activation of collagenase in a mammal. This invention also relates to the use of tenidap and the pharmaceutically-acceptable base salts thereof for treating collagenase mediated disorders and diseases such as bone resorption disorders, corneal ulceration, periodontal disease, inflammatory diseases and wounds of the skin and burns in a mammal. Further, this invention relates to the use of tenidap and the pharmaceutically-acceptable base salts thereof to inhibit the activity of myeloperoxidase in a mammal. The methods of this invention comprise administering an effective amount of tenidap or salts thereof to such a mammal.

2. General Background

Tenidap, 5-chloro-2,3-dihydro-2-oxo-3-(2-thienylcarbonyl)-indole-1-carboxamide, has the structural formula

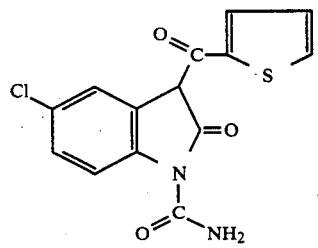

Tenidap and the pharmaceutically-acceptable base salts thereof, among other 3-substituted-2-oxindole-1-carboxamides, are disclosed and claimed in U.S. Pat. No. 4,556,672 which is assigned to the assignee hereof. That patent discloses that those compounds, in addition to being useful as antiinflammatory and analgesic agents, are inhibitors of both the cyclooxygenase (CO) and lipoxygenase (LO) enzymes. The teachings thereof are incorporated herein by reference.

The use of tenidap and its pharmaceutically-acccceptable base salts, among certain other 3-substituted-2-oxindole-1-carboxamides, to inhibit interleukin-1 biosynthesis in a mammal and to treat interleukin-1 mediated disorders and dysfunctions is disclosed in U.S. Pat. No. 4,861,794 which is assigned to the assignee hereof.

U.S. Pat. No. 4,853,409, assigned to the assignee hereof, discloses the use of tenidap and its pharmaceutically-acceptable base salts, among certain other 3-substituted-2-oxindole-1-carboxamides, to suppress T-cell function in a mammal and to treat T-cell mediated autoimmune disorders of the systemic or organ specific type.

An anhydrous, crystalline form of the sodium salt of tenidap is disclosed in European Patent Application 277,738 which has been filed in the name of the assignee hereof.

Collagenase is a protease which is stored within neutrophil specific granules in a latent form. [Hasty, K.A., et al., J. Biol. Chem. 261:5645–5650 (1986) and Hasty, K.A., et al., J. Biol. Chem. 262:10048–10052 (1987).]Collagenase, in its activated form, mediates a variety of disorders and diseases in a mammal. These disorders and diseases include, but are not limited to, bone resorption disorders such as osteoporosis and metastatic bone cancer, corneal ulceration, periodontal disease, inflammatory joint disease, inflammatory diseases and wounds of the skin and burns. [Harris, E.D., et al., NEJM 291:605–609 (1974) and Harris, E.D., et al., NEJM 291:652–660 (1974).]Collagenase can be activated from its latent form by hypochlorous acid. [Weiss, S.J., et al., Science 227:747–749 (1985).]The enzyme myeloperoxidase converts hydrogen peroxide, itself the dismutased product of superoxide radicals, into hypochlorous acid. Once activated, collagenase is capable of irreversibly cleaving collagen of types 1, 2 and 3. [Hasty, D.A., et al., J. Biol. Chem. 262:10048–10052 (1987).]

It has been reported that certain gold compounds can interfere with activated collagenase, but only in the presence of organomercurials. [Mallya, S.K., et al., J. Biol. Chem. 264:1594–1601 (1989) and Mallya, S.K. et al., Biochem. Biophys. Res. Comm. 144:101–108 (1987).]Further, penicillamine has been reported to scavenge hypochlorite and inhibit its formation by myeloperoxidase. [Cuperus, R.A., et al., Arthritis Rheum. 28:1228–1233 (1985).]

However, until the invention herein, there was no report of use or intent to use tenidap or the salts thereof to inhibit the activation of collagenase and to treat collagenase mediated disorders and diseases such as bone resorption disorders, corneal ulceration, periodontal disease, inflammatory diseases of the skin and burns with tenidap nor any appreciation of its role in such treatments. Further, there was no report of use or intent to use tenidap or the salts thereof to inhibit the activity of myeloperoxidase with tenidap nor any appreciation of its ability to inhibit myeloperoxidase in a mammal.

SUMMARY OF THE INVENTION

It has been found that tenidap and the pharmaceutically-acceptable base salts thereof inhibit the activation of collagenase in a mammal and thus are useful in inhibiting the activation of collagenase per se and in treating collagenase mediated disorders and diseases. Such collagenase mediated disorders and diseases include, but are not limited to, bone resorption disorders, corneal ulceration, periodontal disease, inflammatory diseases and wounds of the skin and burns. Further, it has been found that tenidap and its pharmaceutically-acceptable base salts inhibit the activity of myeloperoxidase in a mammal and are useful in inhibiting myeloperoxidase per se.

The method of using tenidap and its pharmaceutically-acceptable base salts comprises administering to a mammal an effective amount thereof. Administration can comprise any known method for therapeutically providing a compound to a mammal such as by oral or parenteral administration as defined hereinbelow.

DETAILED DESCRIPTION OF THE INVENTION

Tenidap, which has the chemical structure

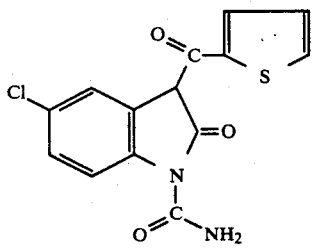

its pharmaceutically-acceptable base salts and the preparation thereof are described in U.S. Pat. No. 4,556,672, the teaching of which are incorporated herein by reference. This invention concerns new uses for tenidap and its salts which comprise inhibiting the activation of collagenase in a mammal and inhibiting the activity of myeloperoxidase in a mammal. Also within the scope of this invention are methods of treating collagenase mediated disorders and diseases in a mammal. Such collagenase mediated disorders and diseases include, but are not limited to, bone resorption disorders such as osteoporosis and metastatic bone cancer, corneal ulceration, periodontal disease, inflammatory diseases and wounds of the skin and burns.

As disclosed in U.S. Pat. No. 4,556,672, tenidap is acidic and forms base salts. All such base salts are within the scope of this invention and can be formed as taught by that patent. Such suitable salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as
triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts. An anhydrous crystalline form of such a sodium salt is disclosed in European Patent Application 277,738, filed in the name of the assignee hereof. The teachings thereof which are incorporated herein by reference.

Also within the scope of this invention are the solvates such as the hemihydrates and monohydrates of the compounds hereinabove described.

The methods of this invention comprise administering tenidap and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral.

Parenteral administration as used herein includes, but is not limited to, intravenous, intramuscular, intraperitoneal, subcutaneous, transdermal and topical including, but not limited to oral lavage and inhalation, administration. While it is generally preferred to administer such compounds and their salts orally, other methods may be preferred depending upon the particular collagenase-mediated disorder or disease being treated.

In general, tenidap and its salts are most desirably administered in doses ranging from about 20 mg up to about 200 mg per day, with a preferred range of about 40 mg to about 120 mg per day, for oral administration and from about 1 mg up to about 200 mg per day for parenteral administration, although variations will still necessarily occur depending upon the weight of the subject being treated. The appropriate dose for inhibiting the activity of myeloperoxidase and/or inhibiting the activation of collagenase in a mammal and for treatment of collagenase mediated disorders and diseases with tenidap and its salts will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the generally preferred mode of administration of tenidap or its pharmaceutically-acceptable base salts is oral, they may be administered parenterally as well. Such parenteral administration may be the preferred mode of administration for the treatment of certain collagenase-mediated disorders or diseases.

For purposes of parenteral administration, solutions of tenidap or a salt thereof in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like.

Specific transdermal flux enhancing compositions are disclosed in European Patent Application 271,983 and European Patent Application 331,382, which have been filed in the name of the assignee of this invention, the teachings of which are incorporated herein by reference. For purposes of topical administration, the dosage form of the particular compound may include, by way of example and not of limitation, solutions, lotions, ointments, creams and gels.

The ability of tenidap to inhibit the activation of collagenase and to inhibit the activity of myeloperoxidase were determined by the procedures described below.

Whole human blood from normal volunteers was obtained by venipuncture into heparinized syringes. The majority of the red cells were removed by dextran sedimentation and neutrophils were separated by density centrifugation over hypaque ficoll. The neutrophil rich fraction was washed and residual red cells were removed by hypotonic lysis according to the procedure described by Blackburn, W.D. et al., Arthritis Rheum. 30:1006-1014 (1987). The neutrophils so prepared were used in the assays described below and cell viability was assured by determining their ability to exclude typan blue. In each assay the cell viability routinely exceeded 95%.

To assay for inhibition of release of activated collagenase by neutrophils, the following assay was performed. Neutrophil cell suspensions were incubated at 37° C. for 15-30 minutes in the presence of varying concentrations of tenidap or other compound under study. Tenidap was dissolved and diluted in water and added to the cells directly therefrom. Other compounds tested were initially dissolved in 0.1M NaOH and then diluted in water prior to addition to the cells. After the cells had been incubated in the presence of tenidap or other compound under study, the cell suspensions (5 × $10^6$ cells/ml, 125 μl/well) were added to IgG coated and bovine serum albumin (BSA) blocked wells of microtiter plates and incubated for 45 minutes at 37° C. As controls, similar incubations were performed in the absence of IgG. Following incubation, the cell suspensions were centrifuged (750 × g) for 5 minutes at 4° C. The supernatants were removed and DFP (diisopropylfluorophosphate) was added to a final concentration of $10^{-3}$M to inactivate serine proteases.

Then, the collagenase activity in the DFP treated supernatants was determined by incubating, in triplicate, 200 μl aliquots of supernatant with $^3$H-labeled reconstituted type-I collagen fibrils in 7 mm flat bottom tissue culture wells (Linbro ®, Cat #76-032-05, Flow Laboratories McLean, Va) as described by Johnson-Wint, B., Anal. Biochem. 104:175-181 (1980). The reconstituted fibrils in each well contained 75 μg of a mixture of $^3$H-labeled and unlabeled collagen with an activity of 7,000 cpm. To determine the total radioactivity potentially released from the fibrils in each experiment, the reconstituted fibrils were also incubated with a mixture of clostridial collagenase (250 mg/ml HBSS (Hank's balanced salt solution, GIBCO, Grand Island, N.Y.)). To maximize sensitivity and specificity of the assay, incubations were performed for eighteen hours in triplicate at 37° C. At the end of the incubation period, the supernatants were aspirated from each well and the radioactivity was determined by counting in a liquid scintillation counter. Greater than 99% of the radioactivity applied to each well was recovered from wells incubated with bacterial collagenase. Average counts per minute released by fibrils incubated with buffer (HBSS) alone were subtracted from the cpm measured in each supernatant. The resulting triplicate values for each supernatant were averaged and divided by the average cpm released by the bacterial collagenase to determine the percent fibril lysis produced by each supernatant. The total activated collagen released during the eighteen hour incubation was then calculated and divided by the incubation time to yield values for the collagenase activity (ng collagen degraded/min) in each supernatant.

In parallel experiments, release of total collagenase into the supernatants was determined by activating latent collagenase in the supernatants with 1.0 mM mersalyl (Harris, E.D. and Vater, C.A., Methodology of collagenase research: substrate purification, enzyme activation and purification. Collagenase in Normal Pathological Connective Tissues. Edited by D. E. Woolley, J. M. Evanson, Chichester, John Wiley & Sons, 1980) prior to addition of the supernatants to the radiolabeled collagen fibrils. To avoid underestimation of total collagenase released due to inhibition of protease activity by oxidative metabolites generated during neutrophil activation, the supernatants used for these determinations were derived from neutrophils activated in the presence of 1.0 mM sodium azide (an inhibitor of myeloperoxidase). Incubations and calculations of collagenase activity in the mersalyl treated supernatants were performed as described above.

Employing the foregoing assay with tenidap, piroxicam, indomethacin, ibuprofen and naproxen, at peak drug concentrations, yielded the data shown in Table I, below.

TABLE I

| | Inhibition of Activated Neutrophil Collagenase Release | |
|---|---|---|
| Compound | Peak Concentration (μM) | % Inhibition |
| Tenidap | 87.5 | 64 |

TABLE I-continued

| | Inhibition of Activated Neutrophil Collagenase Release | |
|---|---|---|
| Compound | Peak Concentration (μM) | % Inhibition |
| Piroxicam | 25 | 18 |
| Indomethacin | 2.5 | 14 |
| Ibuprofen | 175 | 0 |
| Naproxen | 80 | 0 |

As shown in Table I, ibuprofen and naproxen, both cyclooxygenase inhibitors had no inhibitory effect on the release of activated collagenase by neutrophils. Piroxicam and indomethacin, both also cyclooxygenase inhibitors, had some inhibitory effect on the release of activated collagenase, but at supraphysiological concentrations for those compounds. Tenidap, at clinically relevant concentrations, significantly inhibited the release of activated collagenase from neutrophils.

A further assay was conducted wherein neutrophils, prepared as described above, were incubated in the presence and in the absence of tenidap and then stimulated by incubation in the presence of IgG, all as described above. The supernatants were then activated by the addition of organic mercurial mersasyl. As a result of this assay, it was found that tenidap inhibited by 22% the total amount of collagenase released by neutrophils. Thus, it was concluded that tenidap inhibition of the release of activated collagenase is due to inhibition of the activation of collagenase.

The ability of tenidap to inhibit the activity of myeloperoxidase was demonstrated by the following assay. Neutrophils (1.25 × 10$^6$/ml, prepared as described above) were incubated for 60 minutes at 37° C. in either BSA or IgG coated tissue culture wells which had been blocked with BSA. Following incubation, the wells were aspirated and the cells were removed by centrifugation. Separately, myeloperoxidase was extracted from whole neutrophils with b 1M NaCl and separated from cell debris by centrifugation. The supernatants were dialyzed against HBSS. Then, to the dialyzed supernatants were added varying concentrations of tenidap. Myeloperoxidase activity was then determined by adding 20 μl of the supernatant to 300 μl of 0.2M sodium acetate buffer, pH 4.5, containing 17 mg of 2,2′-azino-di-(3-ethylbenzthiazoline)sulfonic acid and 600 μl of 0.003% hydrogen peroxide. The activity of myeloperoxidase in the supernatant was then determined by the change in absorbance at 412 nm using a spectrophotometer as described by Shindler, J.S. et al., Eur. J. Biochem. 65:325-331 (1976).

What is claimed is:

1. A method of inhibiting activation of collagenase in a mammal in need thereof which comprises administering to said mammal a collagenase activation inhibiting amount of tenidap or a pharmaceutically-acceptable base salt thereof.

2. The method according to claim 1 wherein tenidap or a pharmaceutically-acceptable base salt thereof is administered orally.

3. The method according to claim 1 wherein tenidap or a pharmaceutically-acceptable base salt thereof is administered parenterally.

4. A method of treating a collagenase-mediated disorder or disease in a mammal which comprises administering to said mammal a collagenase-mediated disorder or disease treating amount of tenidap or a pharmaceutically-acceptable base salt thereof.

5. The method according to claim 4 wherein tenidap or a pharmaceutically-acceptable base salt thereof is administered orally.

6. The method according to claim 4 wherein tenidap or a pharmaceutically-acceptable base salt thereof is administered parenterally.

7. The method according to claim 4 wherein the collagenase-mediated disorder is bone resorption disorder.

8. The method according to claim 7 wherein the bone resorption disorder is osteoporosis or metastatic bone cancer.

9. The method according to claim 4 wherein the collagenase-mediated disorder or disease is corneal ulceration.

10. The method according to claim 9 wherein tenidap or a pharmaceutically-acceptable base salt thereof is administered topically.

11. The method according to claim 4 wherein the collagenase-mediated disorder or disease is periodontal disease.

12. The method according to claim 10 wherein tenidap or a pharmaceutically-acceptable base salt thereof is administered topically.

13. The method according to claim 4 wherein the collagenase-mediated disorder or disease is an inflammatory disease or wound of the skin in a mammal.

14. The method according to claim 11 wherein tenidap or a pharmaceutically-acceptable base salt thereof is administered topically.

15. A method of treating burns of the skin of a mammal which comprises administering to said mammal a burn treating amount of tenidap or a pharmaceutically-acceptable base salt thereof.

16. The method according to claim 15 wherein tenidap or a pharmaceutically-acceptable base salt thereof is administered orally.

17. The method according to claim 15 wherein tenidap or a pharmaceutically-acceptable base salt thereof is administered parenterally.

18. The method according to claim 17 wherein said parenteral administration comprises administering tenidap or a pharmaceutically-acceptable base salt thereof topically.

19. A method of inhibiting the activity of myeloperoxidase in a mammal in need thereof which comprises administering to said mammal a myeloperoxidase inhibiting amount of tenidap or a pharmaceutically-acceptable base salt thereof.

20. The method according to claim 19 wherein tenidap or a pharmaceutically-acceptable base salt thereof is administered orally.

21. The method according to claim 19 wherein tenidap or a pharmaceutically-acceptable base salt thereof is administered parenterally.

* * * * *